United States Patent [19]

Kurz

[11] 4,248,587
[45] Feb. 3, 1981

[54] ORTHODONTIC TOOL

[76] Inventor: Craven H. Kurz, 10921 Wilshire Blvd., Suite 512, Los Angeles, Calif. 90024

[21] Appl. No.: 86,701

[22] Filed: Oct. 22, 1979

[51] Int. Cl.³ .............................................. A61C 3/00
[52] U.S. Cl. ...................................... 433/4; 433/160; 81/424
[58] Field of Search .................. 433/4, 160, 159, 162, 433/154, 157; 81/424, 350, 351, 379

[56] References Cited

U.S. PATENT DOCUMENTS

| | | | |
|---|---|---|---|
| 681,224 | 8/1901 | Jacob | 433/160 |
| 1,109,096 | 9/1914 | West | 433/154 |
| 1,631,916 | 6/1927 | Chambers | 81/424 |
| 3,208,319 | 9/1965 | Westby et al. | 81/379 |
| 3,986,265 | 10/1976 | Cusato | 433/4 |
| 4,197,647 | 4/1980 | Goldenthal | 433/159 |

FOREIGN PATENT DOCUMENTS 581005  7/1933  Fed. Rep. of Germany ........... 433/160
427695  4/1935  United Kingdom ................... 433/159

OTHER PUBLICATIONS

Dentronix Brochure, 1972, items 160 and 347.
Arista Catalog, 1968, p. 14.

Primary Examiner—Gene Mancene
Assistant Examiner—John J. Wilson
Attorney, Agent, or Firm—Keith D. Beecher

[57] ABSTRACT

A tool in the form of specially constructed plyers for removing orthodontic brackets and tubes which have been adhesively bonded to the labial, buccal or lingual surfaces of the anterior and/or posterior teeth for orthodontic treatment. The tool is equipped with a spring-loaded catch having a tip which fits under the edge of the bracket, and with a head which engages the top of the tooth, so that when the handles of the tool are squeezed together the bonded bracket is removed from the surface of the tooth without any tendency to torque the tooth during the process.

5 Claims, 11 Drawing Figures

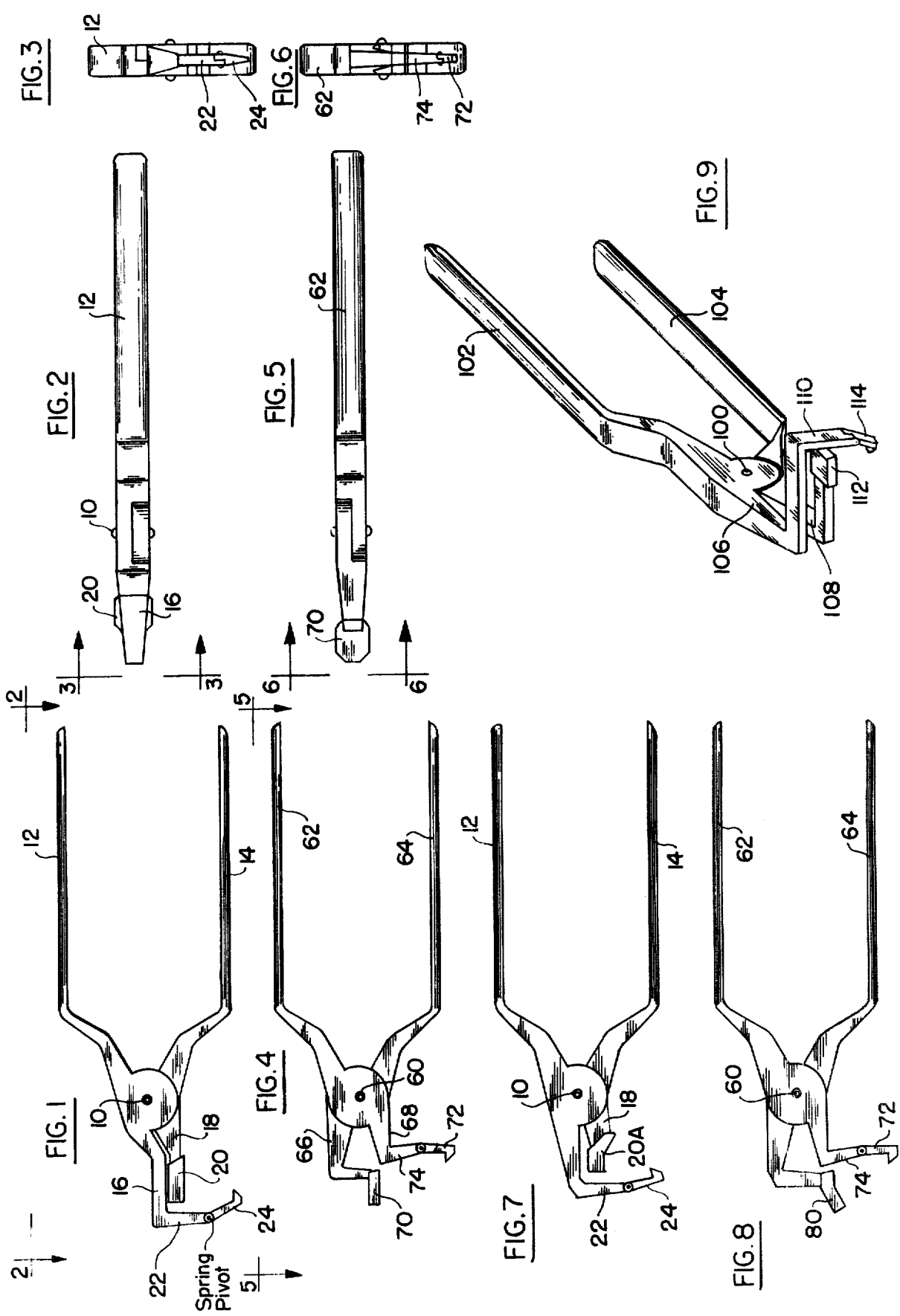

ORTHODONTIC TOOL

BACKGROUND

As is well known, for orthodontic treatment it is the usual practice adhesively to bond brackets and tubes to the labial or buccal surfaces of the patient's teeth. Co-pending application Ser. No. 741,850, filed Nov. 15, 1976, in the name of the present inventor, describes a further orthodontic treatment in which the brackets and tubes are adhesively bonded to the lingual surfaces of the teeth. In either case, and especially in the lingual case, problems arise in effectuating the speedy and easy removal of the adhesively bonded brackets from the surfaces of the teeth after the orthodontic treatment has been completed. The present invention provides a simple and inexpensive tool by which the foregoing may be achieved.

BRIEF DESCRIPTION OF THE DRAWINGS

FIG. 1 is a side view of a tool constructed in accordance with one embodiment of the invention, and which is intended to be used in the removal of orthodontic brackets and tubes which have been adhesively bonded to the lingual side of the patient's teeth;

FIG. 2 is a top view taken along the line 2—2 of FIG. 1;

FIG. 3 is an end view taken along the line 3—3 of FIG. 2;

FIG. 4 is a tool constructed in accordance with a second embodiment of the invention, and which is constructed to remove orthodontic brackets from the labial of the teeth;

FIG. 5 is a top view taken along the line 5—5 of FIG. 4;

FIG. 6 is an end view taken along the line 6—6 of FIG. 5;

FIG. 7 is a view of a tool, similar to the tool of FIG. 1, but one in which the head has been canted so as to reduce any torquing tendency on the tooth as the bonded bracket is being removed from the tooth;

FIG. 8 is a view like FIG. 4, in which the head of the tool has been canted, similar to the head of the tool of FIG. 7;

FIG. 9 is a tool constructed for removing brackets and tubes from the posterior teeth of the patient;

DETAILED DESCRIPTION OF THE ILLUSTRATED EMBODIMENTS

Figure 11:
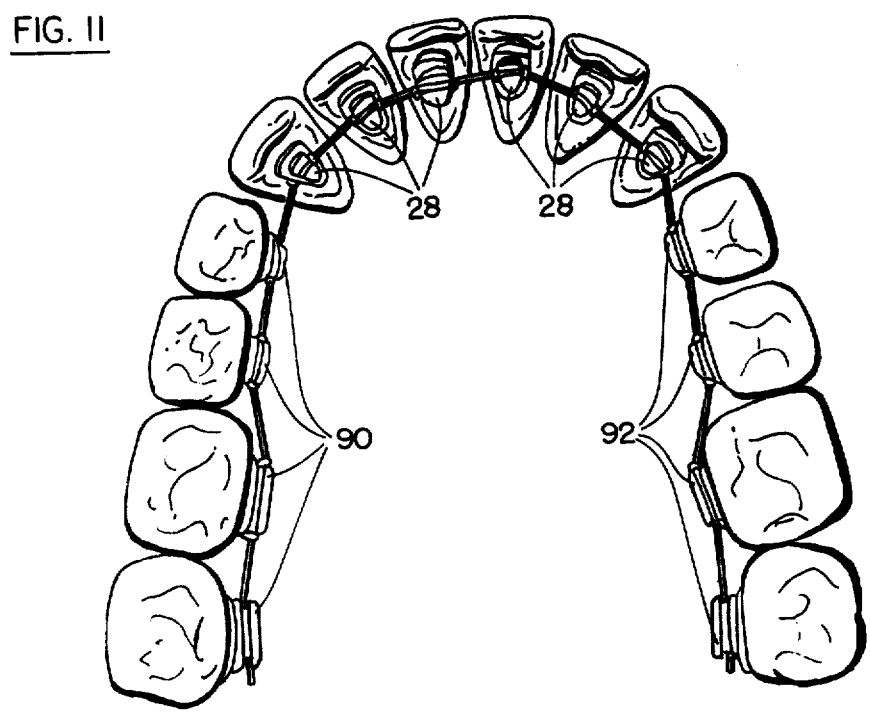
FIG. 11 is a representation of an orthodontic appliance which includes brackets and tubes adhesively bonded to the lingual side of the teeth.

The tool illustrated in FIGS. 1 and 2 and 3 is especially constructed to remove brackets which have been adhesively bonded to the lingual surface of the patient's teeth, such as brackets 30 shown in FIG. 11. The tool has first and second sections which are pivotally coupled by a pin 10 and which define a first handle 12, a second handle 14, a first jaw 16 and a second jaw 18. A head portion 20 is formed on the end of jaw 18, which is the lower jaw of the tool, and a depending portion 22 is formed on the end of jaw 16, which is the upper jaw. The depending portion 22 overhangs the head portion 20, as shown.

A spring-loaded catch 24 is pivotally coupled to the distal end of the elongated portion 22, and is spring biased to the right in FIG. 1, so that it is maintained in contact with the lingual surface of the bracket being removed. The lower end of catch 24 extends under the edge of the bracket, so that when the handles 12 and 14 are squeezed together, the catch 24 grasps the lower edge of the bracket and causes the bracket to be removed from the lingual surface of the tooth.

The representation of FIG. 7 is similar to that of FIG. 1, and like elements have been designated by the same numbers. However, in the embodiment of FIG. 7 the head 20 is replaced by a canted head 20A which is shaped so that any tendency for the tooth to torque while the tool is being operated is obviated.

Figure 10:
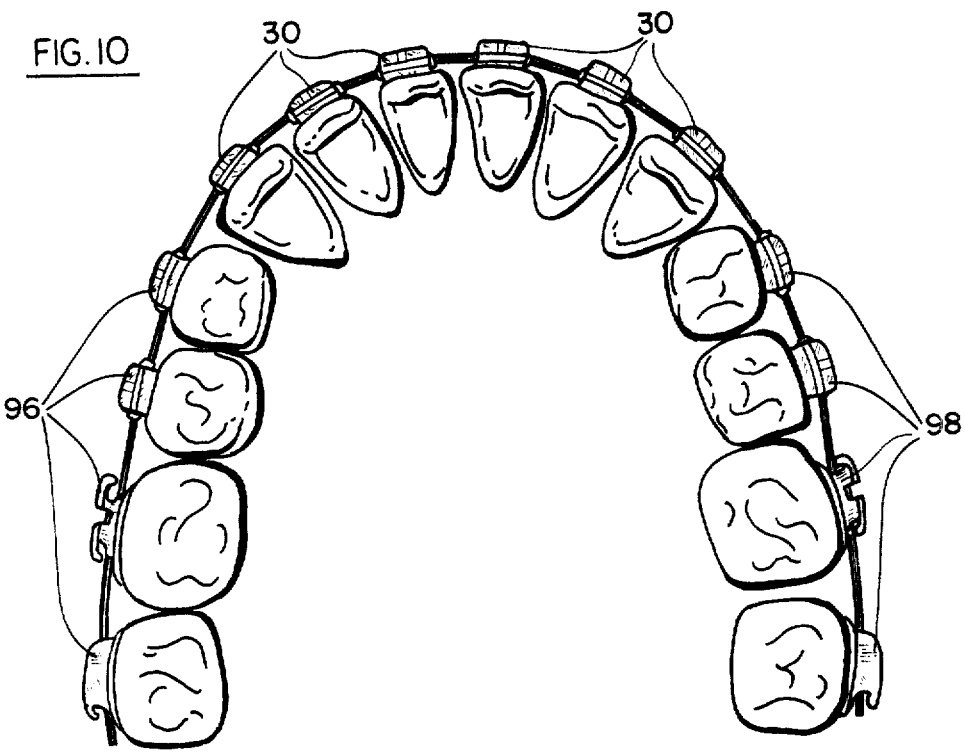
FIG. 10 is a representation of an orthodontic appliance which includes orthodontic brackets and orthodontic tubes adhesively bonded to the labial and buccal side of the teeth.

The tool of FIGS. 4, 5 and 6 is intended to be used to remove brackets from the labial sides of the teeth, such as the brackets 30 of FIG. 10. The tool of FIG. 4 includes first and second sections pivotally coupled by a pin 60 to define a first handle 62 and a second handle 64, and to define an upper jaw 66 and a lower jaw 68. In the tool of FIGS. 4, 5 and 6, a head portion 70 is formed on the upper jaw 66, and a spring-loaded catch 72 is pivotally mounted to the distal end of a depending portion 74 of lower jaw 68. In this case the depending portion extends away from the head portion 70.

The tool of FIGS. 4, 5 and 6 is intended to be used to remove brackets 30 from the labial surfaces of the teeth in FIG. 10, as mentioned above. When so used, the head portion 70 engages the top of a tooth, and the depending portion 74 extends down the front of the tooth so that the end of catch 72 may extend under the edge of the bracket bonded to the labial surface. Then, when the handles 62 and 64 are squeezed, the bracket is forced upwardly and off the tooth.

The tool of FIG. 8 is similar to the tool of FIG. 4, and like elements have been designated by the same numbers. However, in the tool of FIG. 8 head portion 70 is replaced by a canted head portion 80 which is shaped further to reduce any tendency for the tooth to torque while the tool is being operated to remove the bonded bracket from the surface of the tooth.

The tool of FIG. 9 is particularly designed to remove the tubes from the posterior teeth of the patient, such as the tubes 90 in FIG. 11. The tool of FIG. 9 includes first and second portions which are pivotally coupled to one another by a pin 100, to define a first handle 102 and a second handle 104, and also to define an upper jaw 106 and a lower jaw 108. In the embodiment of FIG. 9, an elongated depending portion 110 is formed on the end of upper jaw 106, but is displaced transversely of the longitudinal axis of the tool, as shown. Likewise, a head 112 is formed on the end of lower jaw 108, but likewise is displaced transversely of the longitudinal axis of the tool. As in the previous embodiments, a spring-loaded catch 114 is formed on the end of the depending portion 110.

The tool of FIG. 9 is particularly constructed to remove the tubes from the posterior teeth, such as the tubes 90 in FIG. 11. A similar tool but with the head and catch displaced in the opposite direction may be used to remove the tubes 92 from the lingual surfaces of the right-hand posterior teeth in FIG. 11. Likewise, a similar tool but constructed similar to the tool of FIG. 4 may be used to remove the tubes 96 from the buccal surfaces of the left-hand posterior teeth in FIG. 10, and a similar tool with an opposite offset may be used to remove the right-hand tubes 98 from the buccal surfaces of the posterior teeth in FIG. 10.

The invention provides, therefore, a simple tool which is easy to use, and which provides a convenient means for removing adhesively bonded orthodontic brackets and tubes from a patient's teeth after the orthodontic treatment has been completed.

It will be appreciated that while particular embodiments of the invention have been shown and described, modifications may be made. It is intended in the claims to cover the modifications which come within the spirit and scope of the invention.

What is claimed is:

1. A tool for removing an adhesively bonded orthodontic bracket from the surface of a tooth, which comprises: first and second sections pivotally coupled to one another to define first and second handles and first and second jaws for the tool; a head portion formed on one of the jaws in position to engage the top of the tooth; an elongated depending portion positioned on the other of the jaws; and a spring-loaded catch member pivotally coupled to the distal end of said depending portion in position to be spring biased against the bracket with the end of the catch member extending under the edge of the bracket.

2. The tool defined in claim 1, in which the head portion is canted to permit the bracket to be removed by the tool without excessively torquing the tooth.

3. The tool defined in claim 1, in which the head portion is formed on the lower jaw, and the elongated depending portion is formed on the upper jaw in overhanging relationship with the lower jaw so as to permit the catch member to extend down behind the tooth for the removal of a bracket adhesively bonded to the lingual side of the tooth.

4. The tool defined in claim 1, in which the head portion is formed on the upper jaw, and the elongated depending portion is formed on the lower jaw and extends away from the head portion to permit the catch member to extend down in front of the tooth for the removal of a bracket adhesively bonded to the labial or buccal side of the tooth.

5. The tool defined in claim 1, in which said head portion and said elongated depending portion are displaced from the longitudinal axis of the tool in a transverse direction to permit the tool to be used to remove the bracket from a posterior tooth.

* * * * *